United States Patent [19]

Oki et al.

[11] 4,316,011

[45] Feb. 16, 1982

[54] RHODOMYCIN ANTIBIOTICS

[75] Inventors: Toshikazu Oki, Yokohama; Akihiro Yoshimoto; Yasue Matsuzawa, both of Fujisawa; Taiji Inui, Chigasaki; Tomio Takeuchi; Hamao Umezawa, both of Tokyo, all of Japan

[73] Assignee: Sanraku-Ocean Co., Ltd., Tokyo, Japan

[21] Appl. No.: 164,756

[22] Filed: Jun. 30, 1980

[30] Foreign Application Priority Data

Jul. 13, 1979 [JP] Japan .................................. 54-89552

[51] Int. Cl.$^3$ ...................... C07H 15/24; A61K 31/71
[52] U.S. Cl. .................................. 536/17 A; 424/180
[58] Field of Search ...................................... 536/17 A

[56] References Cited

U.S. PATENT DOCUMENTS

| | | | |
|---|---|---|---|
| 3,988,315 | 10/1976 | Umezawa et al. | 536/17 A |
| 4,039,736 | 8/1977 | Nettleton et al. | 536/17 A |
| 4,127,714 | 11/1978 | Umezawa et al. | 536/17 A |
| 4,144,329 | 3/1979 | Umezawa et al. | 536/17 A |

*Primary Examiner*—Johnnie R. Brown
*Attorney, Agent, or Firm*—Jordan and Hamburg

[57] ABSTRACT

New anthracycline glycoside derivatives of rhodomycin-group, ε-rhodomycin RDC, ε-isorhodomycin RDC, β-rhodomycin RDC, γ-rhodomycin RDC, γ-rhodomycin RDRs and β-pyrromycin RDC having potent anticancer activities and lower toxicities and a process for the production thereof by microbiological conversion method are disclosed.

1 Claim, 6 Drawing Figures

RHODOMYCIN ANTIBIOTICS

BACKGROUND OF THE INVENTION (1) Field of the Invention

The present invention provides novel anthracycline glycoside derivatives belonging to rhodomycin-group, and relates to a process for the production thereof, and more particularly, the present invention relates to the novel derivatives of anthracycline glycoside of the general formula I:

wherein $R^1$ is a hydrogen atom or hydroxyl group, and $R^2$ is a hydrogen atom or the following sugar chain:

—O—rhodosamine-2-deoxyfucose-cinerulose residue and $R^3$ is a hydroxyl group or carbomethoxy(—COOCH$_3$) group or the foregoing sugar chain, —O—rhodosamine-2-deoxyfucose-cinerulose residue, or the following sugar chain: —O—rhodosamine-2-deoxyfucose-rhodinose residue and $R^4$ is a hydrogen atom or hydroxyl group, and to a process for the production thereof.

(2) Description of the Prior Art

A number of anthracycline glycosides have been found in the culture medium of Streptomyces, and described in prior literature. Among them, daunomycin and adriamycin have already been applied clinically for human cancers.

Rhodomycinones, iso-rhodomycinone and rhodomycin-related antibiotics are described in Chem. Ber. 88, 1792–1818 (1955); Chem. Ber. 101, 1341–1348 (1968); J. Med. Chem., 20, 957–960 (1977); Pharmacie 27, 782–789 (1972); Zeit. Allg. Mikrobiol., 14, 551–558 (1974); Tetrahed. Lett. No. 38, 3699–3702 (1973); Folia Microbiol., 24, 293–295 (1979); and J. Antibiotics, 32, 420 (1979).

Aclacinomycin A is disclosed in U.S. Pat. No. 3,988,315 and by Oki et al. in J. Antibiotics 28, 830 (1975) and 32, 791–812 (1979).

Cinerubins A and B are disclosed in U.K. Pat. No. 846,130, U.S. Pat. No. 3,864,480, Keller-Schierlein et al., "Antimicrobial Agents and Chemotherapy," page 68 (1970), Chemical Abstracts 54, 1466i (1960) and J. Antibiotics 28, 830 (1975).

Further illustrative and summary disclosures of anthracycline antibiotics can be located in Index of Antibiotics from Actinomycetes, Hamao Umezawa, Editor-in-chief, University Park Press, State College, Pennsylvania, U.S.A. (1967) as follows:

| Antibiotics | Page numbers |
|---|---|
| Aclacinomycins A and B | 101–102 |
| Adriamycin | 122 |
| Carminomycin I | 225 |
| Galirubins S - D | 405–408 |
| Rhodomycins X - Y | 879–880 |
| β-Rhodomycins | 881–885 |
| γ- Rhodomycins | 886–892 |
| Steffimycin | 945 |

The textbook, Antibiotics, Volume 1, Mechanisms of Action, edited by David Gottlieb and Paul D. Shaw, Springer-Verlag New York, Inc., N.Y. (1967) at pages 190–210 contains a review by A. DiMarco entitled "Daunomycin and Related Antibiotics."

Information Bulletin, No. 10, International Center of Information of Antibiotics, in collaboration with WHO, December, 1972, Belgium, reviews anthracyclines and their derivatives.

In their continuation of a study on biogenesis and biosynthesis of anthracycline antibiotics, especially aclacinomycins produced by Streptomyces galilaeus and rhodomycins produced by Actinomyces roseoviolaceus or Streptomyces purpurascens, the present inventors have developed an unique method for obtaining new anthracycline antibiotics from biologically inactive anthracyclinone by microbial glycosidation, and applied it to the search for useful anthracycline antibiotics having more potent antitumor activity and lower toicity than adriamycin and daunomycin, which are widely used as cancer chemotherapeutic agents. As a result, they found that aclacinomycin-producing microorganisms (Japan Patent Kokoku No. SHO 51-34915, Japan Patent Kokai No. SHO 53-44555, Japan Patent Kokai No. SHO 54-63067), for example, Streptomyces galilaeus MA 144-M1 (ATCC 31133, FERM-P 2455), and mutants therefrom, produced new rhodomycin-group antibiotics from various anthracyclinones such as $\epsilon$-rhodomycinone, $\gamma$-rhodomycinone, $\beta$-rhodomycinone, $\epsilon$-isorhodomycinone and $\epsilon$-pyrromycinone by the microbial glycosidation, confirmed that these antibiotics, named as rhodomycins RDC or RDRs and pyrromycin RDC, are new compounds which have potent antitumor activity and low toxicity in animals, and established the processes and method for their preparation and purification.

OBJECTS OF THE INVENTION

Accordingly, it is an object of this invention to provide new anthracycline glycoside derivatives having potent anticancer activities and lower toxicities.

Another object of the invention is to provide a new process for producing anthracycline glycoside derivatives by microbiological conversion of anthracyclinone to the corresponding anthracycline glycoside.

Still another object of this invention is to provide a pharmaceutical composition for antitumor agents.

SUMMARY OF THE INVENTION

The novel derivatives of rhodomycin-group of antibiotics according to the present invention include the following six compounds:

$\epsilon$-rhodomycin RDC, $\epsilon$-isorhodomycin RDC, $\beta$-rhodomycin RDC, $\gamma$-rhodomycin RDC, $\gamma$-rhodomycin RDRs and $\beta$-pyrromycin RDC wherein
R is rhodosamine, D is 2-deoxyfucose, C is cinerulose and Rs is rhodinose residue, respectively, and $R^1$, $R^2$, $R^3$ and $R^4$ of the formula I have the following combinations of definition in said compounds

|  | $R^1$ | $R^2$ | $R^3$ | $R^4$ |
|---|---|---|---|---|
| $\epsilon$-rhodomycin RDC | —H | -o-r-d-c | —COOCH$_3$ | —OH |
| $\epsilon$-isorhodomycin RDC | —OH | -o-r-d-c | —COOCH$_3$ | —OH |
| $\beta$-rhodomycin RDC | —H | -o-r-d-c | —OH | —OH |
| $\gamma$-rhodomycin RDC | —H | —H | -o-r-d-c | —OH |
| $\gamma$-rhodomycin RDRs | —H | —H | -o-r-d-r | —OH |
| $\beta$-pyrromycin RDC | —OH | -o-r-d-c | —OH | —H | wherein
-o-r-d-c is —O—rhodosamine-2-deoxyfucosecinerulose residue and
-o-r-d-r is —O—rhodosamine-2-deoxyfucoserhodinose and the non-toxic acid addition salts thereof.

Other embodiments of the present invention provide a new process for biological production of $\epsilon$-rhodomycin RDC, $\epsilon$-isorhodomycin RDC, $\beta$-rhodomycin RDC, and $\gamma$-rhodomycin RDC by cultivating a microorganism of streptomyces capable of converting anthracyclinone to corresponding anthracycline glycoside and adding said anthracyclinone to the culture of said microorganism during cultivation to produce and isolate said anthracycline glycoside from the cultured medium.

Still other embodiments of the present invention provide a pharmaceutical containing sufficient amounts of the anthracycline glycoside derivatives of the present invention or non-toxic acid addition salts thereof to inhibit the growth and nucleic acid biosynthesis of malignant tumors, such as L 1210, in mammals.

DETAILED DESCRIPTION OF THE INVENTION

The starting materials of the present invention are biologically inactive anthracyclinone having the formula II:

wherein
$R^1$, $R^{2'}$, $R^{3'}$ and $R^4$ are the following groups:

|  | $R^1$ | $R^{2'}$ | $R^{3'}$ | $R^4$ |
|---|---|---|---|---|
| $\epsilon$-rhodomycinone | —H | —OH | —COOCH$_3$ | —OH |
| $\epsilon$-isorhodomycinone | —OH | —OH | —COOCH$_3$ | —OH |
| $\beta$-rhodomycinone | —H | —OH | —OH | —OH |
| $\gamma$-rhodomycinone | —H | —H | —OH | —OH |
| $\beta$-pyrromycinone | —OH | —OH | —OH | —H |

At present the anthracyclinone used for substrate in the present invention are the above five, which can be prepared by extraction and purification from fermented medium, but if structurally related anthracyclinone are prepared in the future they can be preferably utilized based on the substrate specificity of microbial reaction. Furthermore, not only rhodomycinones but the various structurally related anthracyclinones such as aklavinone, $\epsilon$-pyrromycinone, 10-decarbomethoxyaklavinone, 4-methoxyaklavinone also can be used as presursors to produce novel anthracycline glycosides.

Anthracyclinones as described above can be isolated directly from their cultured mediums or obtained by acid hydrolysis of the corresponding anthracycline glycosides, for example, from aclacinomycin A, aclacinomycin B (U.S. Pat. No. 3,988,315), MA 144 G1, G2, L, N1, S1, S2, U1, U2 (Japan Patent Kokai No. SHO 53-44555), MA 144 Y (Japan Patent Kokai No. SHO 54-63067), roseorubicin A and B (J. Antibiotics 32, 420–424, 1979) and rhodomycins by Actinomyces roseoviolaceus or *Streptomyces purpurascens* (before mentioned).

Microorganisms used for the present invention are aclacinomycin-producing strains such as *Streptomyces galilaeus* MA 144-M1 (ATCC 31133) (FERM-P 2455) and various mutants therefrom obtained by the physical treatment with irradiation such as ultraviolet, $\alpha$-, $\beta$-, $\gamma$- and X-ray, or by the mutation using chemical mutagens such as NTG and diepoxybutane. For example, mutant strain KE 303 (FERM-P 4808) derived from *Streptomyces galilaeus* MA 144-M1 (ATCC 31133) (FERM-P 2455) is most preferably used for the present invention.

As an example of obtaining mutant strains, the spores were obtained from the parent strain grown on YS agar slant, treated by N-methyl-N'-nitro-N-nitrosoguanidine (NTG) at the concentration of 1000 μg/ml after ultrasonic disintegration, harvested, and inoculated onto YS agar medium. Colonies grown on YS agar medium were inoculated in the seed medium, and cultured in the production medium. The resulting mycelium was extracted with organic solvents, and the extract was checked for the productivity of yellow pigment due to aclacinomycins by spectrophotometry. The yellow pigment (anthracycline)-non-producing colonies were selected and then tested for the capability of producing aclacinomycin A from aklavinone by shaking culture in the producing medium containing aklavinone. Thus, the mutant strains possessing ability to produce aclacinomycin A were selected and isolated.

*Streptomyces galilaeus* KE 303 (FERM-P 4808) thus obtained has the following morphological and physiological properties similar to those of the parent strain MA 144-M1, excepting a little difference in the color of substrate mycelium. This mutant, thus, can be defined as a mutant strain incapable of producing pigments. Therefore, other than the newly isolated mutant mentioned above, other mutants derived from aclacinomycin-producing strains, incapable of producing anthracycline pigments and capable of producing anthracycline glycosides from anthracyclinone as substrate, also can be used in the present invention.

The strain KE 303 (FERM-P 4808) has the following properties:

1. Morphological characteristics:

Under a microscope, open spirals well developed from branched substrate mycelia are observed. There are no whorls. The mature spore chain has more than ten spores.

The spores are ellipsoidal, 0.4–0.8×0.7–1.6 μm insides, and their surface is smooth. The strain could not produce any sporangium and sclerotium. The strain was assigned to spirales section in genus Streptomyces.

2. Properties on various media:

The description in parenthesis follows the color standard of the "Color Harmony Manual" published by Container Corporation of America, U.S.A.

(1) On sucrose-nitrate agar, incubated at 27° C.:
White to pale yellow (2 db) growth; no aerial mycelium; no soluble pigment.

(2) On glucose-aspargine agar, incubated at 27° C.:
Pale yellow (1ba) to pale yellow green (1½ec) growth; light gray (d) aerial mycelium; no soluble pigment.

(3) On glycerol-asparagine agar (ISP medium No. 5), incubated at 27° C.:
Pale yellow green (1cb) to light grayish olive (1½ge) growth; yellowish gray to light gray (2dc) aerial mycelium; no soluble pigment.

(4) On starch-inorganic salts agar (ISP medium No. 4), incubated at 27° C.:
Pale yellow (1ba) to pale yellow green (1cb) growth; medium gray (2fe, Covert Gray) to gray (d) aerial mycelium; no soluble pigment.

(5) On tyrosine agar (ISP medium No. 7), incubated at 27° C.:
Light grayish yellowish brown (3ge) to grayish brown (4li) growth; lately observed pale gray aerial mycelium; black soluble pigment.

(6) On nutrient agar, incubated at 27° C.:
Grayish yellow (3ec) growth, yellowish gray (2dc) to light gray (d) aerial mycelium; brown soluble pigment.

(7) On yeast extract-malt agar (ISP medium No. 2), incubated at 27° C.:
Pale olive (2gc) to pale yellowish green (1½ ec) growth; light brownish gray (3fe, Silver gray to dark gray 3ih, Beige gray) aerial mycelium; no soluble pigment or slightly brownish soluble pigment.

(8) On oatmeal agar (ISP medium No. 3), incubated at 27° C.:
Pale yellow (2db) to grayish yellow (3ec) growth; yellowish gray (2dc) to light gray (d) aerial mycelium, brown soluble pigment.

3. Physiological Properties:

(1) Growth temperature was examined on maltose-yeast extract agar (maltose 1.0%, yeast extract (Oriental Yeast KK) 0.4%, agar 3.5%, (pH 6.0)) at 20, 24, 27, 30, 37 and 50° C. Optimal temperature for the growth is 27° C. to 37° C. but no growth at 50° C.

(2) Gelatin liquefaction (15% gelatin, incubated at 20° C.; and glucose-peptone-gelatin agar, incubated at 27° C.):
In case of simple gelatin medium, gelatin liquefaction was obeseved as weak at 14 days incubation, but, in glucose-peptone-gelatin agar medium, as weak or moderate after 7 days incubation.

(3) Starch hydrolysis on starch-inorganic salts agar at 27° C.:
Weak hydrolysis was observed after 5 days incubation.

(4) Peptonization and coagulation of skimmed milk at 37° C.:
Moderate to stron peptonization began after 5 days incubation and finished after around 17 days. No coagulation.

(5) Melanin formation on tryptone-yeast extract medium (ISP medium No. 1); peptone-yeast extract-ferrous agar (ISP medium No. 7) incubated at 27° C. The formation of melanin-like pigment was positive.

(6) Utilization of carbon sources on Pridham-Gottlieb basal medium (ISP medium No. 9), incubated at 27° C.:
Abundant growth with L-arabinose, D-xylose, glucose, D-fructose, sucrose, inositol, L-rhamnose and raffinose; no growth with D-mannitol.

(7) Liquefaction of calcium malate on calcium malate agar at 27° C.
Calcium malate was strongly liquefied.

(8) Nitrate reduction on peptone medium containing 1% sodium nitrate (ISP medium No. 8), incubated at 27° C.:
Positive.

The above mutant in the present invention was deposited in the Fermentation Reseach Institutue, Japan as *Streptomyces galilaeus* KE 303, and added to their culture collections of microorganisms as FERM-P 4808.

Fermentative production of the compounds in the present invention is carried out by cultivating an anthracycline-non-producing strain capable of converting exogenous anthracyclinones to anthracycline glycosides according to the conventional fermentation process used for microorganisms belonging to the genus Streptomyces and adding corresponding anthracyclinone to the cultured media during the cultivation.

The media preferably contain commercially available products such as glucose, glycerol, starch, dextrin, sucrose, maltose, fats and oils as carbon sources; soybean powder, cotton seed cake, meat extract, peptone, dried yeast, yeast extract, corn steep liquor etc. as organic nitrogen sources; ammonium sulfate, sodium nitrate, ammonium chloride etc. as inorganic nitrogen sources; and, if necessary, sodium chloride, potassium chloride, phosphates, magnesium salts, heavy metal salts, and vitamins as trace elements can be used.

Submerged aerobic cultivation is preferably employed for the production, and can be carried out within the range of 20° C. to 38° C., and the preferred range of cultivation temperature is from 25° C. to 32° C.

The following procedure is provided as an example for fermentation and isolation of the compounds in the present invention.

The streptomyces culture grown on agar slant, for example, containing 0.3% yeast extract, 1.0% soluble starch, 1.5% agar and having pH 7.0 and stored at 6° to 7° C. is shakecultured for 1 to 2 days at 25° to 32° C. in an aqueous medium consisting of glucose, organic nitrogen sources and inorganic salts to prepare the seed culture. Then, the above seed culture is inoculated 1 to 3% in volume to an aqueous medium, for example, consisting of sucrose, glucose, soybean meal, and inorganic slats, and aerobically cultivated at 25° to 32° C. for 24 to 72 hours. During cultivation, anthracyclinone such as γ-rhodomycinone, ε-isorhodomycinone, β-rhodomycinone, ε-rhodomycinone and β-pyrromycinone at the concentration of 10 to 200 μg/ml is added as a substrate to the medium on the logarithmic growth phase, and the cultivation is further continued for 12 to 72 hours to complete the microbial conversion. Cultured medium thus obtained is centrifuged to separate mycelium from filtrate, and pigments are extracted from mycelium and purified as follows. To extract the compounds of the present invention, acetone, chloroform, methanol, toluene and acidic buffer solution can be used. Purification can be favorably carried out by adsorption column chromatography using silicic acid, and ion-exchange column chromatography using, for example, CM-cellulose (carboxymethyl cellulose, Brown Co.) and gel filtration using Sephadex LH-20 (crosslinked dextran gels Pharmacia Fine Chemical AB). Chemical structure of the compounds thus obtained in the present invention was determined as follows by ultraviolet and visible absorption (abbreviated as UV), infrared absorption (IR), 100 MHz proton and $^{13}$C-NMR and mass spectral analyses, and also by spectral analyses of the anthracyclinone and sugar moieties obtained by acid hydrolysis.

For example, when ε-rhodomycinone was used as substrate for microbial conversion, ε-rhodomycin RDC having the formula III was obtained. ε-Isorhodomycin RDC (Formula IV), β-rhodomycin RDC (Formula V) and β-pyrromycin RDC (Formula VIII) were obtained from ε-isorhodomycinone, β-rhodomycinone and β-pyrromycinone, respectively. γ-Rhodomycinone gave both γ-rhodomycin RDC (Formula VI) and γ-rhodomycin RDRs (Formula VII).

-continued (IV)

(V)

-continued (VI)

(VII)

(VIII)

The compounds in the present invention can be obtained as free base or non-toxic acid addition salts with a variety of organic and inorganic salt-forming reagents. Thus, acid addition salts can be formed with such acids as sulfuric, phosphoric, hydrochloric, bromic, nitric, acetic, propionic, maleic, oleic, citric, succinic, tartaric, fumaric, glutamic, pantothenic, laurylsulfonic, methansulfonic, naphthalenesulfonic and related acids. For use as anticancer agent, free base form of the compounds is equivalent to their non-toxic acid addition salts. Free base of the compounds can be lyophilized with non-toxic acid in the proper solution or acid addition salts can be recovered by precipitation from solvents capable of dissolving slightly their non-toxic acid addition salts. These acid addition salts can be changed in original free base form by neutralizing with basic compounds, and vice versa.

Figure 1:
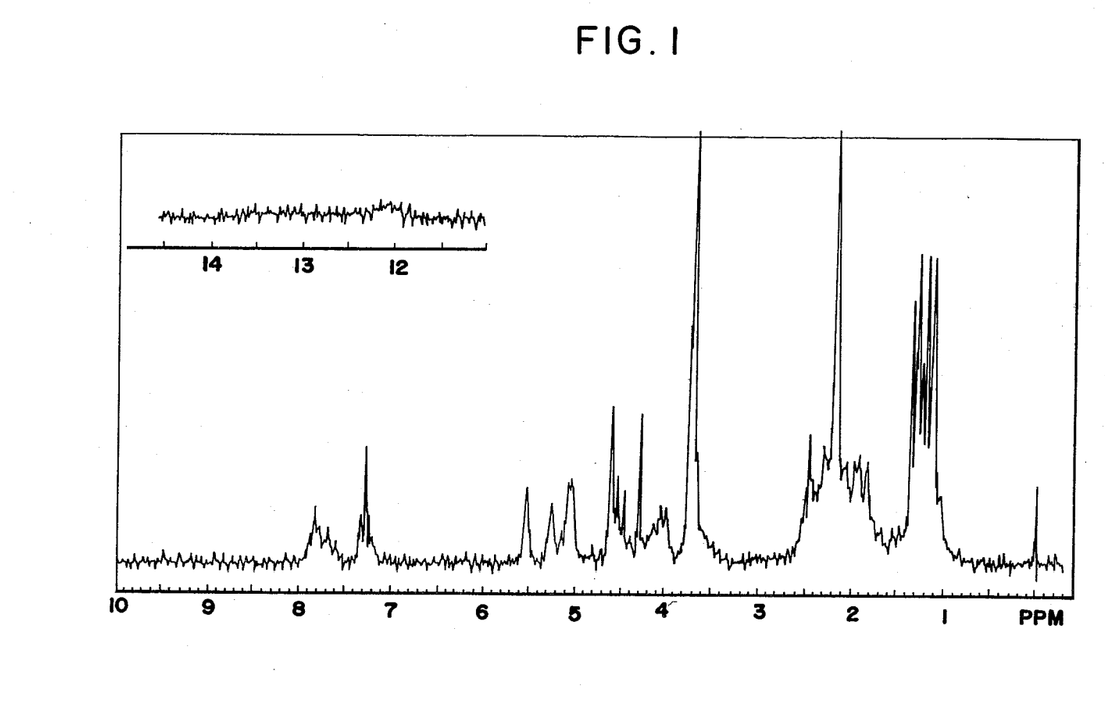
FIGS. 1, 2, 3, 4, 5 and 6 show the PMR spectra in CDCl$_3$ of $\epsilon$-rhodomycin RDC, $\epsilon$-isorhodomycin RDC, $\beta$-rhodomycin RDC, $\gamma$-rhodomycin RDC, $\gamma$-rhodomycin RDRs and $\beta$-pyrromycin RDC, respectively.
Figure 2:
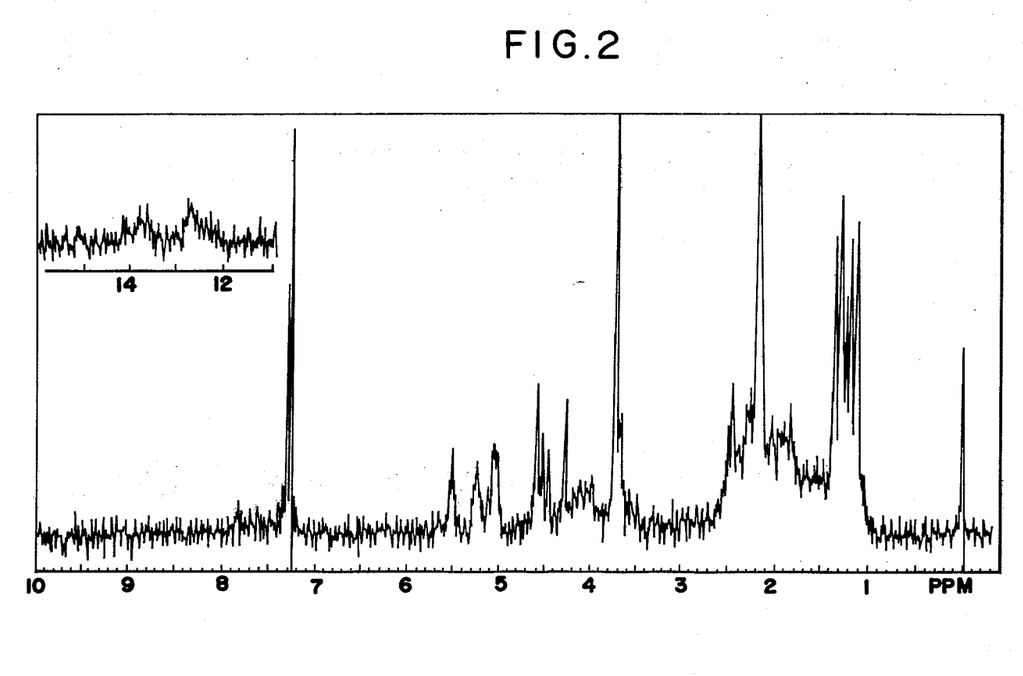
Figure 3:
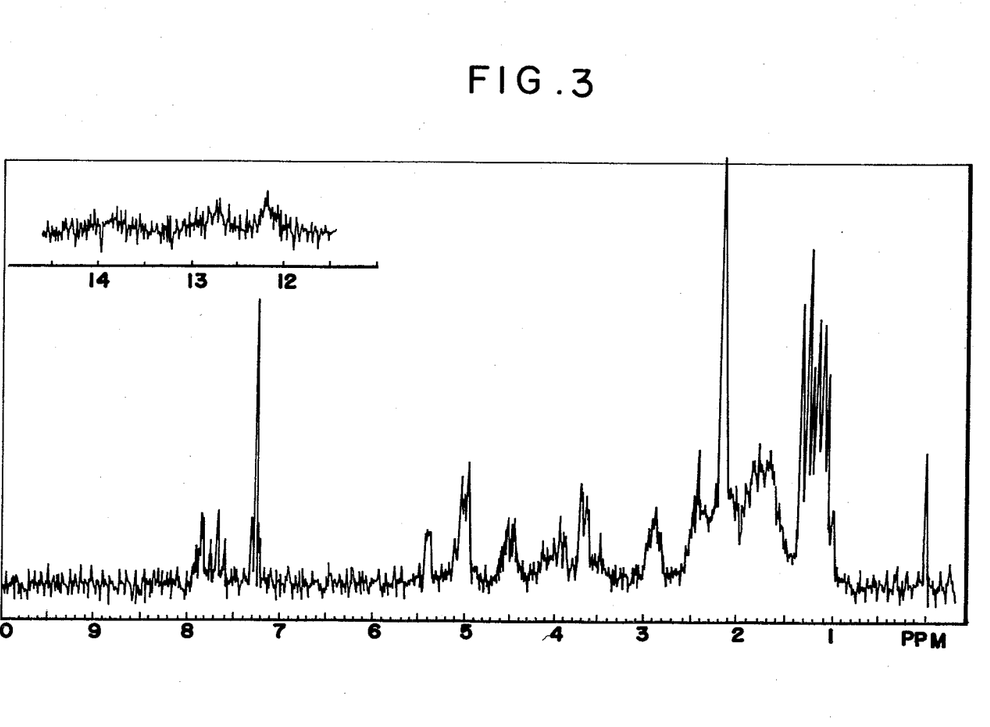
Figure 4:
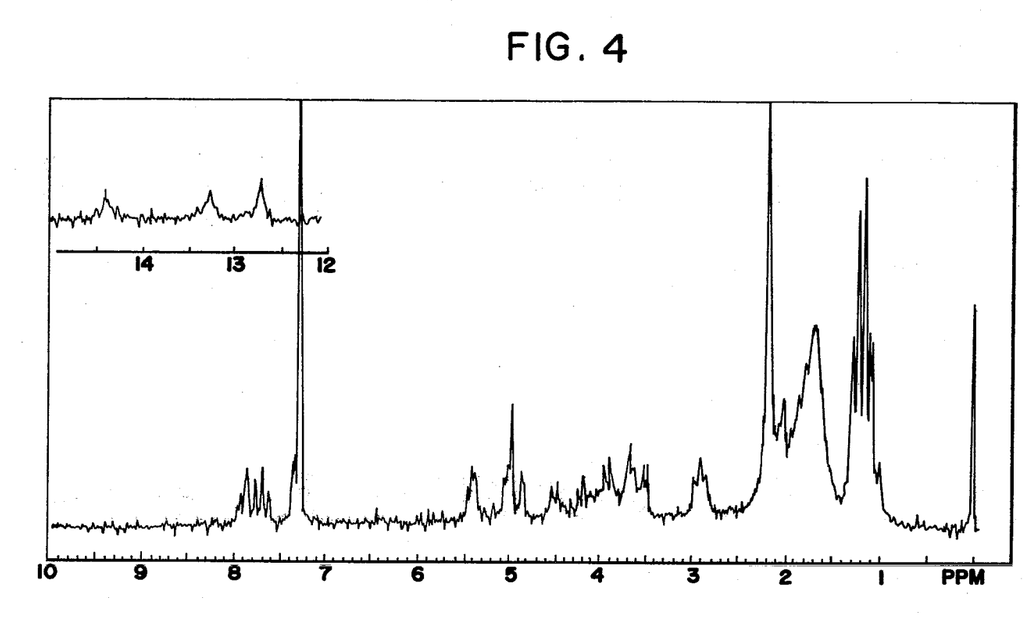
Figure 5:
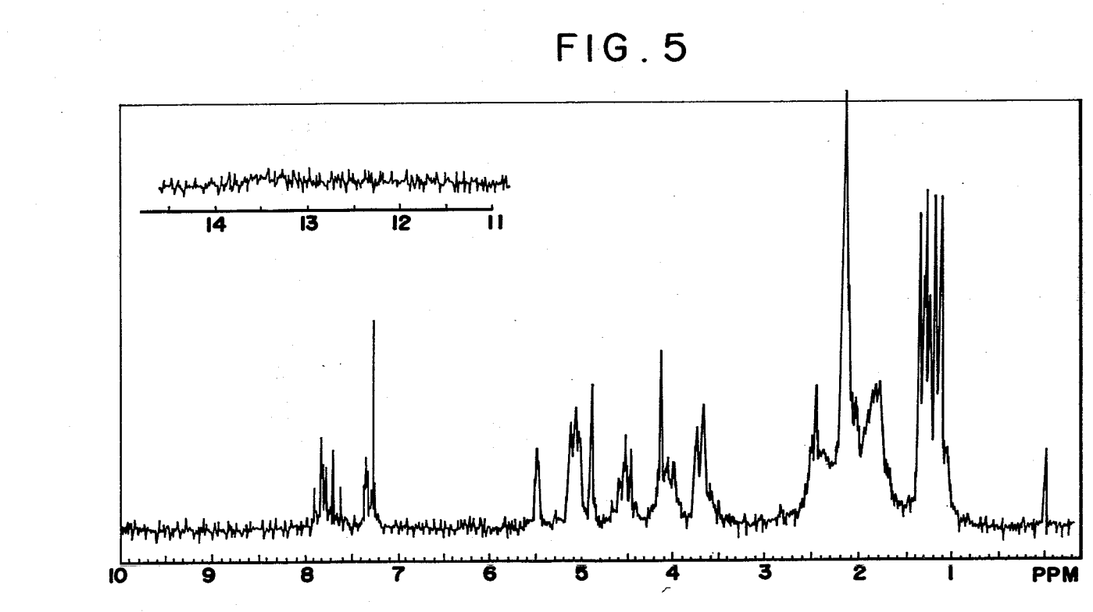
Figure 6:
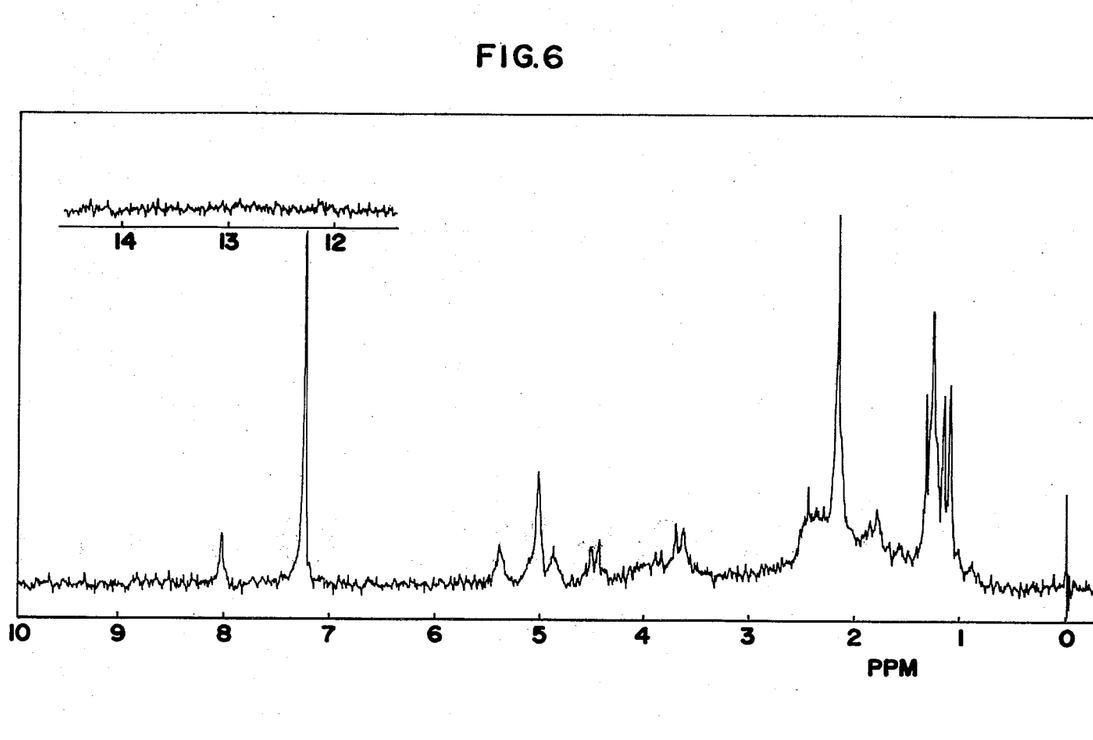

The following are physiocochemical properties of the compounds in the present invention:

| Compound | III | IV | V | VI | VII | VIII |
|---|---|---|---|---|---|---|
| Melting point (°C.) | 160–162 | 162–164 | 163–165 | 143–145 | 139–142 | 128–135 |
| UV and visible absorption spectrum | 235(513) | 240(508) | 235(502) | 236(431) | 236(380) | 234(496) |
|  | 255(307) | 295( 90) | 252(315) | 254(384) | 254(344) | 256(265) |
| $\lambda_{nm}^{max}(E_{1cm}^{1\%})$ | 292(102) | 490s(123) | 292( 98) | 295( 98) | 295( 86) | 290(106) |
|  | 492(184) | 521(184) | 495(183) | 495(196) | 495(174) | 492(132) |
|  | 527s(118) | 547(175) | 528(136) | 528(150) | 528(133) | 512(102) |
| 90% methanol | 585s( 14) | 560(187) | 580( 30) | 560s(33) | 560s(30) | 526( 84) |
|  |  | 605( 48) |  |  |  |  |
| 0.1N HCl-90% methanol | 235(526) | 240(555) | 234(530) | 236(468) | 236(418) | 234(504) |
|  | 255(319) | 295( 98) | 254(330) | 254(400) | 254(362) | 256(265) |
|  | 292(106) | 490s(145) | 290(105) | 295(106) | 295( 96) | 290(106) |
|  | 492(191) | 521(210) | 495(198) | 495(201) | 495(180) | 492(143) |
|  | 527s(119) | 547(185) | 528(135) | 528(148) | 528(132) | 514(115) |
|  |  | 559(194) | 570s(14) | 560s(30) | 560s(25) | 526( 93) |
|  |  | 605( 48) |  |  |  |  |
| 0.1N NaOH-90% methanol | 242(555) | 243(585) | 241(595) | 242(591) | 242(525) | 235(433) |
|  | 287( 99) | 280s(95) | 285(107) | 290(108) | 290s(98) | 296( 88) |
|  | 566(222) | 589(229) | 565(220) | 558(232) | 558(198) | 560(141) |
|  | 605(194) | 632(261) | 600s(175) | 592(200) | 592(177) | 597(127) |
| PMR spectrum | FIG. 1 | FIG. 2 | FIG. 3 | FIG. 4 | FIG. 5 | FIG. 6 |
| IR spectrum (KBr) cm$^{-1}$ | 3475,2940 | 3450,2940 | 3450,2950 | 3425,2940 | 3450,2950 | 3420,2930 |
|  | 1730,1600 | 1730,1590 | 1730,1600 | 1730,1600 | 1605,1445 | 1730,1595 |
|  | 1440,1400 | 1450,1435 | 1440,1400 | 1445,1400 | 1400,1300 | 1440,1285 |
|  | 1290,1240 | 1400,1300 | 1300,1240 | 1295,1255 | 1260,1210 | 1215,1160 |
|  | 1195,1165 | 1260,1190 | 1200,1170 | 1205,1170 | 1170,1120 | 1120,1100 |
|  | 1120,1010 | 1170,1120 | 1120,1010 | 1120,1100 | 1005 | 1010 |
|  |  | 1010 | 1000 | 1015 |  |  |
| Appearance | red powder | red powder | red powder | red powder | red powder | dark red |
| *Rf value (1) | 0.73 | 0.71 | 0.55 | 0.54 | 0.25 | 0.41 |
| Solvent (2) | 0.37 | 0.31 | 0.25 | 0.25 | 0.07 | 0.08 |

| Compound | III | IV | V | VI | VII | VIII |
| --- | --- | --- | --- | --- | --- | --- |
| (3) | 0.43 | 0.42 | 0.32 | 0.34 | 0.20 | 0.06 |

*Silica gel thin-layer (Kieselgel 60F, Merck Co.)
Solvent:
(1)Chloroform:Methanol (10:1, vol)
(2)Chloroform:Methanol:Formic acid (100:10;1, vol)
(3)Benzene:Ethylacetate:Methanol:formic acid:water
 (5:5:1:0.3, vol)

The following describes usefulness of the compounds in the present invention.

(1) The compounds in the present invention inhibited markedly the growth and nucleic acid biosynthesis of murine leukemic L 1210 cells in culture. In an example, L 1210 cells were inoculated in RPMI (Rosewell Park Memorial Institute) 1640 medium containing 20% calf serum at the cell density of $5\times10^4$ cells/ml, and the compound in the present invention was simultaneously added to the medium at the concentration of 0.1 and 0.5 μg/ml and incubated at 37° C. in a $CO_2$ incubator. 50% growth inhibition concentration of the compound over controls was determined. L 1210 cells as described above were also inoculated at $5\times10^5$ cells in RPMI 1640 medium containing 10% calf serum and incubated at 37° C. for 1 to 2 hours in a $CO_2$ incubator. The cells were cultured for 15 min. at 37° C. after the compounds according to the present invention at various concentrations were added, and then $^{14}$C-uridine (0.05 μCi/ml) or $^{14}$C-thymidine (0.05 μCi/ml) was added and incubated for further 60 min. at 37° C. After stopping the pulse-labeling by addition of 10% trichloroacetic acid (TCA) solution to the reaction mixture, acid-insoluble materials were precipitated, washed three times with 5 to 10% TCA, and dissolved in a small amount of formic acid. Then, radioactivity was determined, and inhibitory effects on the DNA and RNA biosynthesis were indicated by the 50% inhibition concentration ($IC_{50}$) of the incorporation of radioactivity over controls. The results are shown in the following table.

| Compound | $IC_{50}$ (μg/ml) | | | Inhibition ratio DNA/RNA |
| --- | --- | --- | --- | --- |
| | Growth | DNA synthesis | RNA synthesis | |
| ε-Rhodomycin RDC | 0.01 | 0.7 | 0.08 | 8.8 |
| ε-Isorhodomycin RDC | 0.007 | 1.25 | 0.11 | 11.1 |
| β-Rhodomycin RDC | 0.01 | 0.57 | 0.15 | 3.8 |
| γ-Rhodomycin RDC | 0.11 | 0.85 | 0.28 | 3.0 |
| γ-Rhodomycin RDRs | 0.09 | 0.7 | 0.3 | 2.3 |
| β-Pyrromycin RDC | 1.0 | 2.0 | 1.5 | 1.3 |

(2) The compounds in the present invention showed the marked inhibitory effects on experimental animal tumors. Antitumor action was most significantly demonstrated in L 1210 leukemia in mice. For example, when $CDF_1$ mice weighing 18 to 22 grams were inoculated with $1\times10^6$ cells of L 1210 cells intraperitoneally and the compound was administered intraperitoneally once daily for 10 days consecutively 24 hours after inoculation, the survival time of mice was over 200% by T/C(%) at optimum dose as shown in the following table. On the other hand, their $LD_{50}$ values against mice upon a single intravenous injection were more than 28 mg/kg, and thus their acute toxicity was much lower than that of adriamycin, which gave 14.2 mg/kg.

Antitumor effect and acute toxicity in mice

| Compound | Opt. dose (mg/kg/day) | T/C (%) | $LD_{50}$ (i.v.) (mg/kg) |
| --- | --- | --- | --- |
| ε-Rhodomycin RDC | 2 | 240 | 32.5 |
| ε-Isorhodomycin RDC | 2 | 235 | 28.2 |
| β-Rhodomycin RDC | 2 | 306 | 28.0 |
| γ-Rhodomycin RDC | 2 | 209 | 39.8 |
| γ-Rhodomycin RDRs | 2 | 203 | 40.6 |
| ε-Pyrromycin RDC | 20 | 202 | 85.5 |
| Adriamycin | 1 | 286 | 14.2 |

As mentioned above, the compounds in the present invention are useful anticancer agents with their characteristic inhibitory action, since ε-rhodomycin RDC, ε-isorhodomycin RDC and β-rhodomycin RDC suppressed the growth of murine leukemic cells at extremely low concentration, and ε-rhodomycin RDC and ε-isorhodomycin RDC inhibited specifically RNA synthesis of L 1210 cells. The following provides for the illustrative preparation procedure of anthracyclinones used in the Example below.

Example

A preparation of anthracyclinones used as substrate

Anthracyclinones as substrate in the present invention can be prepared as follows:

Actinomyces roseoviolaceus IFO 13081 capable of producing roseorubicins A and B was shake-cultured in the seed medium consisting of 0.3% yeast extract and 1% soluble starch, pH 7.0 (100 ml/500-ml Erlenmeyer flask) for 3 days.

Two hundred and fifty 500-ml flasks containing 50 ml of the sterilized production medium consisting of 4% sucrose, 2.5% soybean meal, 0.1% yeast extract, 0.25% sodium chloride, 0.32% calcium carbonate, 0.0005% $CuSO_4.7H_2O$, 0.0005% $MnCl_2.4H_2O$ and 0.0005% $ZnSO_4.7H_2O$, (pH 7.4) (%: wt/vol%) were inoculated respectively with 1 ml each of the seed culture, and shake-cultured for 5 days at 28° C. on a rotary shaker (210 rpm). The resulting cultured medium was centrifuged to separate mycelium and supernatant fluid. Mycelium was extracted with 2 liters of acetone, concentrated and reextracted with 1 liter of chloroform, and the supernatant fluid was extracted with 2 liters of chloroform, combined with the extract from mycelium, and concentrated to dryness to obtain crude substance. Crude substance was dissolved in 70 ml of methanol and the insoluble materials were centrifuged off. The supernatant fluid was applied onto a cross-linked dextran gel (Pharmacia Fine Chemical AB, Sephadex LH-20) (φ4.0×40 cm), eluted with methanol, and fractionated to obtain the initial glycoside fraction and following anthracyclinone fraction. The glycoside fraction was concentrated to dryness; 200 ml of 3.0 N hydrochloride acid were added; and hydrolysis was effected for 1 hour at 85° C. Hydrolysate was extracted with 500 ml of chloroform, and concentrated to obtain crude anthracyclinones containing γ-rhodomycinone, β-rhodomycinone and β-pyrromycinone. The crude anthracyclinones were spotted on preparative thin-layers (60 PF$_{254}$, E. Merck & Co.) and developed with the solvent system of chloroform:methanol (20:1 vol.), and the bands showing R$_f$s 0.53, 0.44 and 0.34 corresponding to γ-rhodomycinone, β-rhodomycinone and β-pyrromycinone were respectively scratched off. Each anthracylinone was extracted from silica gel with the mixture of chloroform-methanol (5:1 vol.), concentrated to dryness, dissolved in a small amount of methanol, and chromatographed with methanol using a cross-linked dextran gel (before mentioned) (φ1.5 cm×50 cm). There were obtained 130 ml of γ-rhodomycinone, 68 mg of β-rhodomycinone and 43 mg of β-pyrromycinone. On the other hand, the above mentioned anthracyclinone fraction (on page 26, line 23) was concentrated to dryness, spotted onto preparative thin-layer, and developed with the solvent system of benzene-acetone-formic acid (100:20:1 vol.). The bands corresponding to ε-rhodomycinone and ε-isorhodomycinone showing R$_f$ values at 0.75 and 0.70, respectively, were scratched off and extracted separately with a mixture of chloroform-methanol (5:1 vol.). Each extract was concentrated to dryness, chromatographed on a cross-linked dextran gel (before mentioned) column as mentioned above, and 28 mg of ε-rhodomycinone, and 32 mg of ε-isorhodomycinone were obtained. Physicochemical properties of the resultant anthracyclinones coincided fully with those of authentic samples in the absorption spectra of UV, IR, mass and NMR, elementary analysis, melting point and R$_f$ values on silicic acid thin layer, and with those values published in the literature (Chem. Ber. 100, 3578–3587 (1967) for ε-rhodomycinone, ε-isorhodomycinone and β-rhodomycinone; Tetrahedron (London) 19, 395–400 (1963) for ε-rhodomycinone). On the other hand, β-pyrromycinone is a new anthracyclinoe having the following physicochemical properties:

Physicochemical Properties of β-Pyrromycinone:
  Melting point: 193°–198° C.
  Mol. Wt.: 386 (Mass spectrum, M+)
  Elementary analysis: $C_{20}H_{18}O_8$

|  | C | H | O |
|---|---|---|---|
| Calcd. (%) | 62.18 | 4.70 | 33.13 |
| Found (%) | 62.02 | 4.82 | 33.41 |

UV and visible absorption spectra:

| | |
|---|---|
| $\lambda_{max}^{90\%MeOH}$ nm($E_{1cm}^{1\%}$): | 233(1173), 256(579), 290(212), 491(359), 511s(282), 525s(230) |
| $\lambda_{max}^{90\%MeOH-0.1N\ HCl}$ nm($E_{1cm}^{1\%}$): | 233(1315), 256(672), 290(243), 491(389), 510s(311), 525s(247) |
| $\lambda_{max}^{90\%MeOH-0.1N\ NaOH}$ nm($E_{1cm}^{1\%}$): | 235(1053), 290s(205), 511(358), 593s(276) |

IR (KBr) spectrum, cm$^{-1}$: 3400, 2900, 1595, 1440, 1280, 1220

Mass spectrum: 386 (M$^{30}$), 368 (M+—H$_2$O)

PMR spectrum (100 Hz, CDCl$_3$): δ ppm: 1.04, t, CH$_2$—CH$_3$; 1.75, q, J=7 Hz, CH$_2$-CH$_3$; 2.13, d, J=5 Hz, CH$_2$-8; 4.74, s, CH-7 & CH-10; 7.95, s, CH-11 7.35, s, CH-2 & CH-3; hydrogen bonded phenolic hydroxyls (12.1, 12.7 & 12.9)

The following example is provided for illustrative purpose only and is not intended to limit the scope of the invention.

EXAMPLE 1

A nutrient medium having the following composition was prepared:

| Soluble starch | 1.5 | wt/vol % |
|---|---|---|
| Glucose | 1.0 | wt/vol % |
| Soybean meal | 1.0 | wt/vol % |
| Yeast extract | 0.1 | wt/vol % |
| NaCl | 0.3 | wt/vol % |
| K$_2$HPO$_4$ | 0.1 | wt/vol % |
| MgSO$_4$ . 7H$_2$O | 0.1 | wt/vol % |
| CuSO$_4$ . 5H$_2$O | 0.007 | wt/vol % |
| FeSO$_4$ . 7H$_2$O | 0.001 | wt/vol % |
| MnCl$_2$ . 4H$_2$O | 0.0008 | wt/vol % |
| ZnSO$_4$ . 7H$_2$O | 0.0002 | wt/vol % |
| pH | 7.4 | |

One hundrend ml of this medium was sterilized in a 500-ml Erlenmeyer flask which was inoculated respectively from an agar slant culture of *Streptomyces galilaeus* KE 303 by platinum loop, and incubated for 48 hours at 28° C. on a rotary shaker. Fifteen hundred 500-ml flasks containing 50 ml of the previously sterilized medium consisted of the same composition as above except for the soybean meal being increased to 3% were respectively inoculated by 1 ml of the seed culture, and cultivated for 20 hours at 28° C. on a rotary shaker (210 rpm). After dividing into five groups of flasks, to 300 flasks of the first group were added 2 ml of ε-rhodomycinone solution (500 μg/ml) in methanol (final concentration of substrate: 20 μg/ml in flask). In the same manner, β-rhodomycinone, ε-isorhodomycinone, γ-rhodomycinone and β-pyrromycinone were added respectively to the other groups of flasks, and cultivation was continued for 24 hours. Respective cultured medium was centrifuged to harvest the mycelium, and respective products were extracted twice from mycelium with 2 liters of acetone. After concentrating the acetone extract to one third volume under reduced pressure, pigments were reextracted with chloroform and concentrated to dryness. The crude conversion product was dissolved in 500 ml of methanol, and insoluble materials were removed by centrifugation. The supernatant methanol solution was introduced onto a cross-linked dextran gel (before mentioned) column (3.5 cm×40 cm) and eluted with methanol. Initial pigment fraction was collected, concentrated to dryness, dissolved in a small amount of chloroform, spotted on preparative thin-layers (kiesalgel 60 PF$_{254}$, E. Merck & Co.) and developed in a mixture of chloroform-methanol (20:1 vol.).

The band corresponding to the conversion product was scratched off, eluted with chloroform-methanol (5:1 vol.), and concentrated to dryness to obtain red crude preparation. This red preparation was dissolved in 10 ml of toluene, shaken vigorously with 10 ml of 0.1 M acetate buffer (pH 3.0) containing 2 mM ethylene diaminetetraacetic acid and the conversion product was transferred to acidic aqueous layer. The aqueous layer was adjusted to pH 7.0 with 1 N NaOH aqueous solution, reextracted with chloroform, dried over sodium sulfate anhydride and concentrated under reduced pressure. n-Hexane was added to the concentrate, and resulting red precipitate was filtered and dried in vacuo to obtain pure compound. The conversion products from other anthracyclinone were extracted from the cultured medium and purified by the same procedure as for ε-rhodomycin RDC, and 57 ml of ε-rhodomycin RDC, 27 mg of ε-isorhodomycin RDC, 48 ml of β-rhodomycin RDC, 18 mg of γ-rhodomycin RDC, 14 mg of γ-rhodomycin RDRs and 24 mg of β-pyrromycin RDC were obtained respectively.

What is claimed is:

1. New derivatives of rhodomycin-group of antibiotics selected from the group consisting of ε-rhodomycin RDC, ε-isorhodomycin RDC, β-rhodomycin RDC and γ-rhodomycin RDC wherein

R is rhodosamine, D is 2-deoxyfucose and C is cinerulose, respectively having the general formula I:

wherein a substitution of R¹, R², R³ and R⁴ represents hydrogen,  and hydroxyl, respectively, or hydroxyl, , carbomethoxy and hydroxyl, or hydrogen, , hydroxyl and hydroxyl, or hydrogen, hydrogen,  and hydroxyl, or a non-toxic acid addition salt thereof.

* * * * *